(12) United States Patent
Armstrong-Muntner et al.

(10) Patent No.: US 8,976,250 B2
(45) Date of Patent: Mar. 10, 2015

(54) LENS INSPECTION SYSTEM

(75) Inventors: Joel S. Armstrong-Muntner, San Mateo, CA (US); James J. Dudley, Sunnyvale, CA (US); Richard Ruh, Monte Sereno, CA (US); Anant Rai, San Jose, CA (US)

(73) Assignee: Apple Inc., Cupertino, CA (US)

( * ) Notice: Subject to any disclaimer, the term of this patent is extended or adjusted under 35 U.S.C. 154(b) by 106 days.

(21) Appl. No.: 13/597,704

(22) Filed: Aug. 29, 2012

(65) Prior Publication Data

US 2013/0293726 A1 Nov. 7, 2013

Related U.S. Application Data

(60) Provisional application No. 61/640,872, filed on May 1, 2012.

(51) Int. Cl.
*H04N 17/00* (2006.01)
*G01M 11/02* (2006.01)
*G01M 11/00* (2006.01)

(52) U.S. Cl.
CPC ............ *G01M 11/02* (2013.01); *G01M 11/005* (2013.01)
USPC ........... 348/180; 348/187; 348/188; 348/181; 348/189; 356/124

(58) Field of Classification Search
CPC ..... H04N 17/00; H04N 17/045; H04N 17/02; G01M 11/02; G01M 11/005; G01M 11/0264
USPC .......... 348/180, 181, 187, 188, 189; 356/124, 356/610, 445
See application file for complete search history.

(56) References Cited

U.S. PATENT DOCUMENTS

| 6,047,082 A | 4/2000 | Rhody et al. |
| 6,195,159 B1 | 2/2001 | MacDonald et al. |
| 6,788,401 B1 | 9/2004 | Kitabayashi et al. |
| 7,308,157 B2 | 12/2007 | Safaee-Rad et al. |
| 7,649,628 B2 | 1/2010 | Wadman |
| 2012/0293808 A1* | 11/2012 | Parks et al. .................... 356/610 |

* cited by examiner

*Primary Examiner* — Jefferey Harold
*Assistant Examiner* — Jean W Desir
(74) *Attorney, Agent, or Firm* — Treyz Law Group; G. Victor Treyz; Kendall P. Woodruff

(57) ABSTRACT

A lens testing system may have a test pattern source that generates a test pattern of light. A lens may have a lens surface that reflects the test pattern of light. A digital camera system may capture an image of the reflected test pattern of light. Computing equipment may perform image processing operations to evaluate the captured image of the reflected test pattern. The test pattern may contain a known pattern of test elements such as a rectangular array of spots or test elements of other configurations. During image processing operations, the computing equipment may analyze the reflected version of the spots or other test elements to measure characteristics of the lens such as radius of curvature, whether the lens contains flat regions, pits, or bumps, lens placement in a support structure, and other lens performance data. The computing equipment may compare the measured lens data to predetermined criteria.

21 Claims, 20 Drawing Sheets

LENS INSPECTION SYSTEM

This application claims the benefit of provisional patent application No. 61/640,872, filed May 1, 2012, which is hereby incorporated by reference herein in its entirety.

BACKGROUND

This relates to optical inspection, and, more particularly, to optical inspection systems for evaluating optical components such as lenses.

Electronic devices such as cellular telephones, computers, and other equipment are often provided with electrical components that use lenses. For example, proximity sensor modules and camera modules may contain lenses.

Compact lenses for components such as these may be manufactured in high volume using techniques such as plastic molding techniques. Due to manufacturing variations, not all lenses may be formed perfectly. Some lenses may contain flattened areas and other imperfections. These imperfections can be difficult or impossible to detect using conventional visual inspection techniques. As a result, there is a risk that defective lenses will be assembled into electrical components. If care is not taken, components may be fully assembled or even used in finished electronic devices before lens problems are detected, leading to waste and manufacturing inefficiencies.

It would therefore be desirable to be able to provide improved ways in which to evaluate lenses.

SUMMARY

A lens testing system may have a test pattern source that generates a test pattern of light. A lens may have a lens surface that reflects the test pattern. A digital camera system may capture an image of the reflected test pattern. Computing equipment may perform image processing operations on the captured image of the reflected test pattern to evaluate the lens.

The test pattern may contain a known pattern of test elements such as a rectangular array of spots or other test elements. For example, the test pattern may contain a series of parallel lines or crisscrossing lines that form a grid. Circular spots, rectangular spots, crosses, or test elements of other shapes may be used. Test elements may be arranged in a rectangular array, in a line, in a circle, or in other suitable patterns. Test patterns may contain circular features such as ring-shaped test elements. Ring-shaped test elements may be nested inside each other in a concentric fashion. Ring-shaped elements may also be arranged in a circular array pattern.

During image processing operations, the computing equipment may analyze the reflected version of the spots or other test elements in a test pattern to measure characteristics of the lens such as radius of curvature. The image processing operations may reveal whether the lens contains defects such as flat regions, pits, or bumps. Lens placement problems such as offsets from a desired location within a support structure may also be detected. Lens faults can be detected when spots in a test pattern are spaced differently than expected, when the number of counted spots in a captured image does not match an expected value, when reflected lines or spots have a different curvature than expected, and when reflected elements have shapes that deviate from expected shapes. Upon detection of a fault, the computing equipment may notify an operator, may create an entry in a data log, or may automatically take corrective action by adjusting manufacturing equipment. Satisfactory lenses may be incorporated into components for use in an electronic device. Faulty lenses may be discarded or reworked.

The testing system may be used to test structures that include plastic lenses, glass lenses, nano-lenses (e.g., lenses of the type that may be used in a field of microscopic lenses resting directly on an image sensor in a light field camera), nano-spheres, other optical structures, or other structures of interest.

Further features of the invention, its nature and various advantages will be more apparent from the accompanying drawings and the following detailed description of the preferred embodiments.

DETAILED DESCRIPTION

Figure 1:
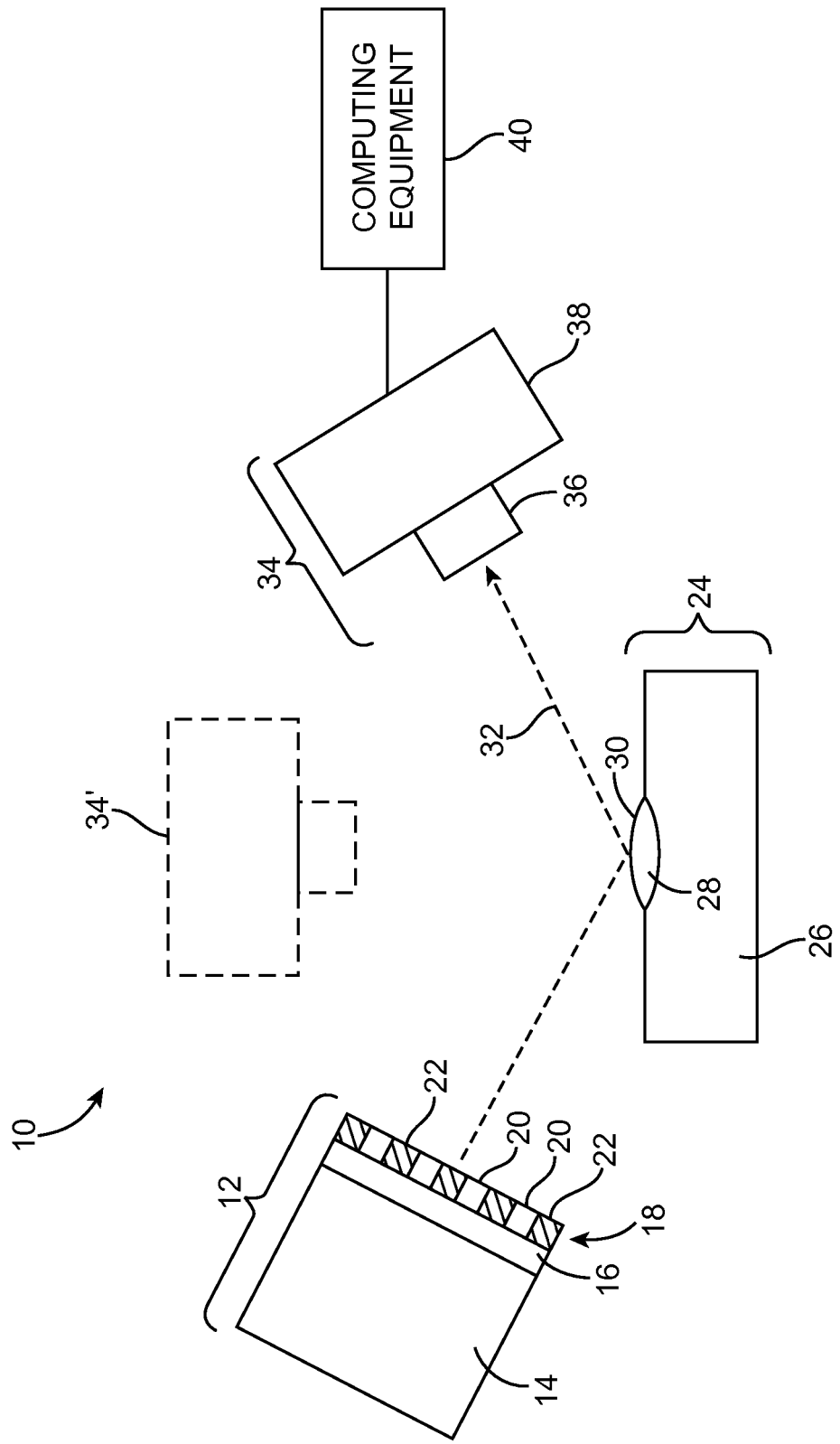
FIG. 1 is a diagram of an illustrative lens inspection system in accordance with an embodiment of the present invention.

An optical inspection system of the type that may be used in inspecting components in an electronic device is shown in FIG. 1. As shown in FIG. 1, optical inspection system 10 may include an illuminated test pattern source such as illuminated test pattern source 12. Test pattern source 12 may include a light source such as light source 14, an optical diffuser such as diffuser 16, and a patterned opaque mask such as mask 18. Light source 14 may be a lamp, one or more light-emitting diodes, or other source of light. Light source 14 may be configured to produce infrared light, visible light, or ultraviolet light.

The light produced by light source 14 may be diffused using light diffuser 16. Light diffuser 16 may be formed from frosted glass, translucent plastic, or other suitable light diffuser structures.

Patterned opaque mask 18 may include an opaque substrate such as opaque mask substrate 22. Openings 20 may be formed in substrate 22. Light may pass through the pattern formed by openings 20. This light may serve as an illuminated test pattern for testing a structure under test in system 10 such as structure under test 24.

Structure under test 24 may include an optical structure or other structures. As an example, structure under test 24 may include a lens such as lens 28 mounted in support structure 24. Support structure 24 may be a test fixture for use during testing of lens 28 or may be a housing or other structure that is part of a component in which lens 28 is to be used. Lens 28 may, if desired, have a diameter that is less than 5 mm, less than 2 mm, less than 1 mm, less than 0.5 mm, or more than 3 mm (as examples). Lens 28 may be formed from molded plastic, glass, or other transparent materials.

Lens 28 may be a visible light lens that passes visible light (and that passes or blocks infrared light and/or ultraviolet light), an infrared (IR) light lens that passes infrared light while passing or blocking infrared light and/or ultraviolet (UV) light, or may be an ultraviolet light lens that passes UV light while allowing visible and/or infrared light to pass or while blocking visible and/or infrared light (as examples).

As shown in FIG. 1, light associated with light test pattern 32 (e.g., a lens test pattern of light produced by a lens test pattern generator such as lens test pattern generator 12 of FIG. 1), may reflect off of exposed surface 30 of lens 28 and may be detected using camera system 34. Camera system 34 may include a lens such as lens 36 and a digital image sensor such as sensor 38. Using lens 36, camera system 34 may view surface 30 of lens 28 or may otherwise capture an image of light reflected from the surface of the structures being tested by system 10. Camera system 34 may be located to one side of structures under test 24, as shown in FIG. 1, or may be located vertically above structures under test 24, as shown by illustrative camera system 34'.

Computing equipment 40 may be used to perform digital image analysis on captured images from camera system 34 to determine whether lens 28 or other structures under test contain defects. Computing equipment 40 may include one or more computers, networked computers, an image processing board in a computer or computer network, an image processing integrated circuit, and/or other equipment for analyzing captured digital image data. If desired, image inspection operations may also be performed manually (e.g., by allowing a user to view a captured image from camera system 34 on a monitor or by providing a microscope through which the user can directly view surface 30).

Structures under test 24 may be any structures with a surface to be inspected. As an example, structures under test 24 may be a fully or partly assembled electronic device component such as a proximity sensor containing an infrared light source, an infrared lens through which infrared light from the infrared light source passes to illuminate an external object, an infrared light detector, and an infrared lens through which infrared light passes that has reflected from the external object. The infrared lenses in this type of component may have surfaces such as surface 30 to be inspected. The lenses may exhibit a transmittance that is larger at infrared wavelengths than visible wavelengths (as an example). This may help ensure that visible light that enters lens 28 will be absorbed by the bulk material that forms lens 28, rather than being reflected back into camera system 34, thereby reducing unwanted reflections from inside structures under test 24 that might potentially interfere with inspection of surface 30 of lens 28. In configurations in which structures under test 24 contain lenses with other optical properties, the wavelength of light produced by light source 14 can be selected accordingly. For example, in configurations in which lens 28 transmits visible light, light source 14 may be configured to produce an out-of-band test pattern such as an ultraviolet test pattern or an infrared test pattern.

Figure 2:
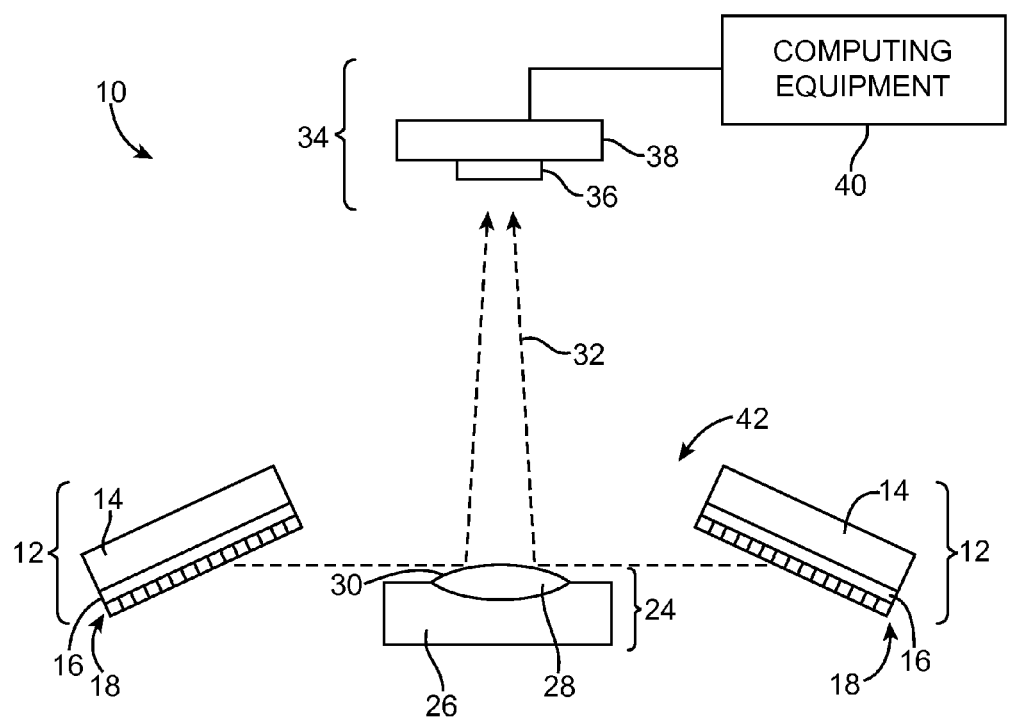
FIG. 2 is a cross-sectional view of a lens inspection system in which a lens is being illuminated using a ring-shaped test pattern source in accordance with an embodiment of the present invention.

As shown in the illustrative configuration of FIG. 2, test pattern source 12 may have a ring-shaped configuration. With this type of arrangement, an opening such as opening 42 may be formed in the center of test pattern source 12. Test pattern source 12 may be pointed downwards. Camera system 34 may be aligned with opening 42 above structures under test 24. Light 32 from ring-shaped test pattern source 28 may illuminate surface 30 of lens 28 and, after passing through opening 42, may be imaged by camera system 34. Computing equipment 40 may analyze the reflected light (light 32) that is detected by camera system 34.

Figure 3:
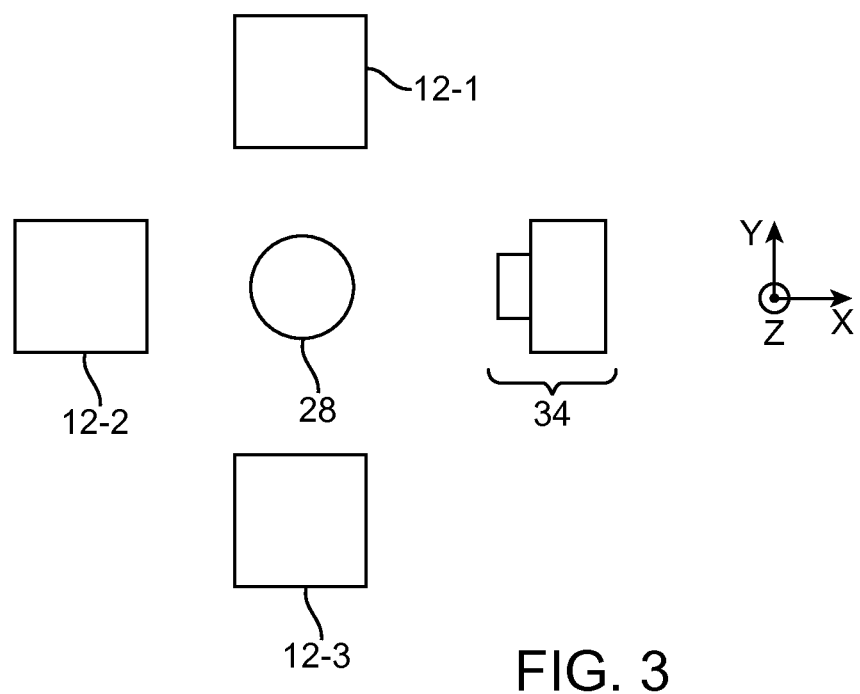
FIG. 3 is a top view of an illustrative lens inspection system showing potential locations within the system at which light sources and a camera may be placed relative to a lens under test in accordance with an embodiment of the present invention.

Another illustrative configuration for system 10 is shown in FIG. 3. FIG. 3 is a top view of system 10 showing how test pattern source 12 may be located in various angularly distributed positions around lens 28 (i.e., test pattern source 12 need not be located directly across from camera system 34). As shown in FIG. 3, illustrative positions that may be used for test pattern source 12 when illuminating lens 28 include positions 12-1, 12-2 (directly across from camera system 34 and raised vertically out of the page in dimension Z above the X-Y plane of lens 28 so that light reflects from surface 30 of lens 28 as shown in FIG. 1), and 12-3. In positions such as position 12-2 and, if desired, positions 12-1 and 12-3, test pattern source 12 may be located slightly above lens 28 in dimension Z to help ensure that light 32 will reflect towards camera system 34 so that camera system 34 can capture images of the test pattern on surface 30 of lens 28.

Figure 4:
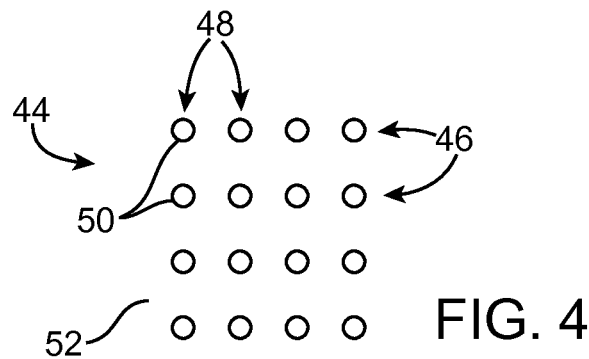
FIG. 4 is an illustrative lens test pattern having a rectangular array of circles in accordance with an embodiment of the present invention.

The pattern of light that is produced by patterned mask 18 of test pattern source 12 may form an array of spots of light or other illuminated test elements or may have other suitable patterns. FIG. 4 is a diagram of an illustrative test pattern based on an array of spots. As shown in FIG. 4, test pattern 44 may include test elements such as circular spots 50 arranged in a rectangular array (i.e., an array containing rows 46 and columns 48 of spots 50). Test elements such as spots 50 are illuminated, whereas background region 52 of pattern 44 is dark.

During testing of lens 28, test pattern source 12 may direct the light of test pattern 44 of FIG. 4 onto surface 30 of lens 28. While test pattern source 12 is illuminating surface 30 of lens 28 using test pattern 44 of FIG. 4, camera system 34 may capture an image of the test pattern reflecting from surface 30 for analysis by computing equipment 40.

Figure 5:
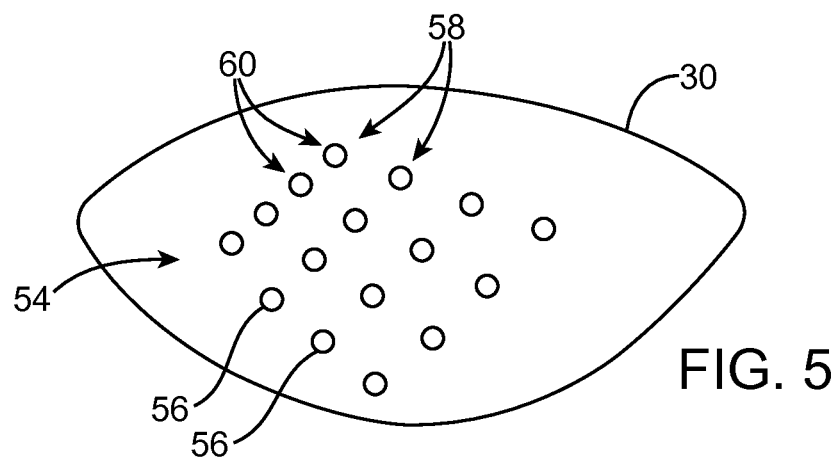
FIG. 5 is an illustrative lens test pattern reflected from the surface of a satisfactory lens in accordance with an embodiment of the present invention.

When test pattern 44 of FIG. 4 reflects from a lens that is free of defects, the image captured by camera system 34 of surface 30 may appear as shown in captured pattern 54 of FIG. 5. Individual test elements such as circular spots 50 may appear distinct and evenly distributed over surface 30. Rows and columns 58 and 60 may be resolved and the spacing between adjacent rows and adjacent columns may be smooth and regular.

Figure 6:
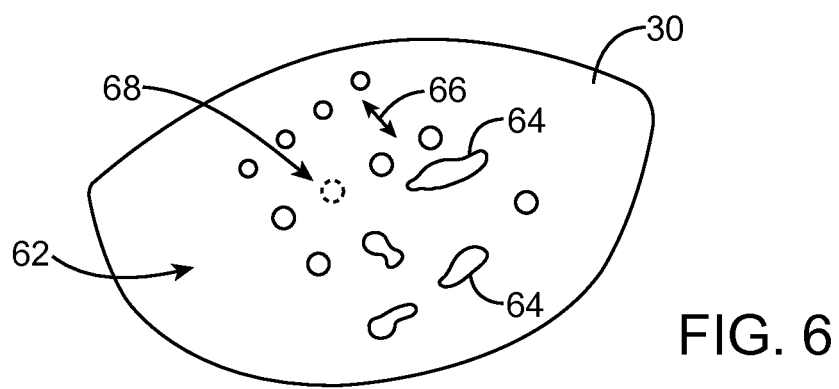
FIG. 6 is an illustrative lens test pattern reflected from the surface of a lens with an imperfection in accordance with an embodiment of the present invention.

In contrast, the reflected test pattern from a defective lens will contain artifacts. When, for example, test pattern 44 of FIG. 4 is reflected from a lens that contains faults, camera system 34 may capture an image such as the image of FIG. 6. In captured pattern 62 of FIG. 6, the light spots of the original test pattern have been reflected unevenly, resulting in a defect-revealing row-to-row (column-to-column) spacing such as spacing 66, reduced-intensity (or missing) spots such as spot 68, smeared out and merged spots such as spots 64, and test pattern features that are otherwise distorted by the surface imperfections of lens surface 30. During image analysis by computing equipment 40, the irregularities that are detected in the captured image of the test pattern may be analyzed to identify the nature of the lens imperfections. As an example, the type of each imperfection may be identified, the severity of each imperfection may be quantified, the location of each imperfection can be identified, the number of imperfections can be quantified, etc.

Figure 7:
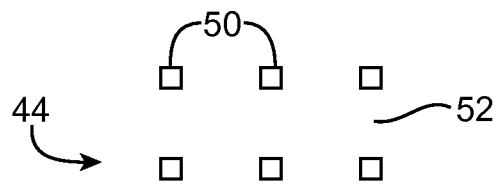
FIG. 7 is an illustrative lens test pattern having a rectangular array of squares in accordance with an embodiment of the present invention.

The rectangular array of circular spots that are used in the illustrative test pattern of FIG. 4 is merely illustrative. In general, test pattern source 12 may generate any suitable test pattern of light. FIG. 7 shows an example in which test pattern 44 includes rectangular (e.g., square) spots 50 in a rectangular array. Spots 50 of FIG. 7 and the other illustrative test patterns described herein may each have the same intensity or may have different intensities (e.g., different known intensities).

Figure 8:
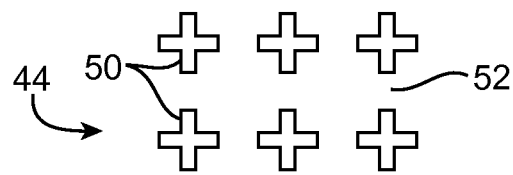
FIG. 8 is an illustrative lens test pattern having a rectangular array of crosses in accordance with an embodiment of the present invention.

To help identify localized imperfections such as small pits or bumps, it may be desirable to provide each test element in the test pattern with additional structure. As shown in FIG. 8, for example, test pattern 44 may include test elements 50 that have the shapes of crosses. During inspection operations, the shape of each reflected cross may be analyzed by computing equipment 40. Well-shaped and properly positioned crosses in the captured image may be indicative of properly formed local regions of lens surface 30. Ill-formed and improperly positioned crosses in the captured image may be used to identify the locations of individual surface defects.

Figure 9:
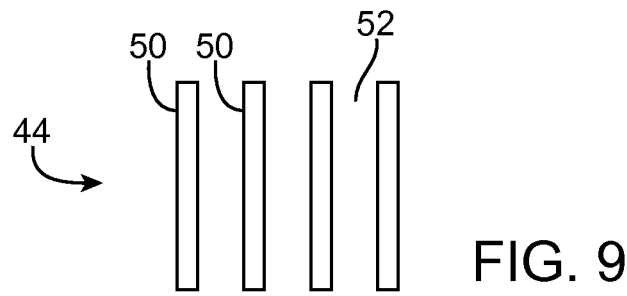
FIG. 9 is an illustrative lens test pattern formed from parallel lines in accordance with an embodiment of the present invention.
Figure 10:
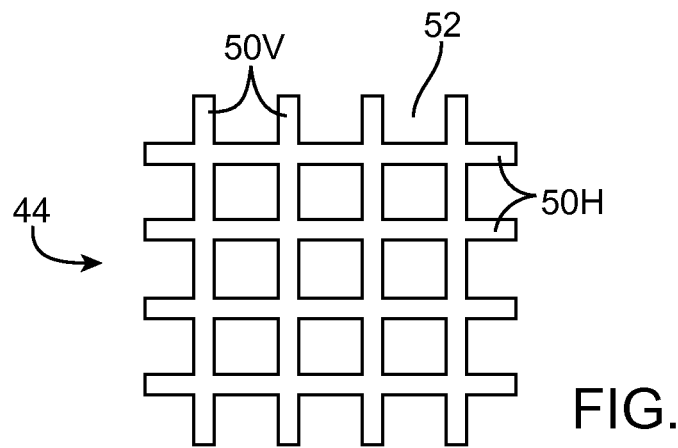
FIG. 10 is an illustrative lens test pattern having a grid of lines in accordance with an embodiment of the present invention.

In the example of FIG. 9, test elements 50 have the shape of parallel lines. FIG. 10 is an example of a test pattern having both horizontal and vertical lines. As shown in FIG. 10, test pattern 44 of FIG. 10 may have vertical lines 50V that overlap and run perpendicular to horizontal lines 50H to form a grid of lines.

Figure 11:
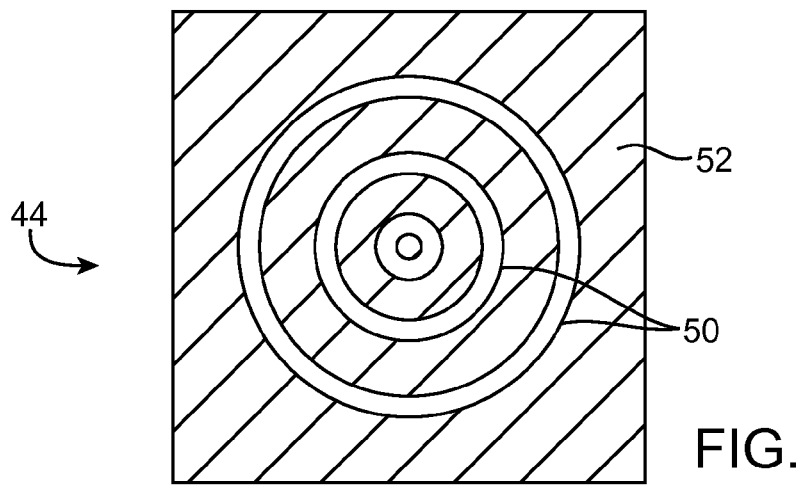
FIG. 11 is an illustrative lens test pattern having concentric rings of light in accordance with an embodiment of the present invention.

In the example of FIG. 11, test pattern 44 includes test elements that have the shape of rings. As shown in FIG. 11, rings 50 may have different diameters, so that each ring may nest within the next to form a set of concentric rings. If desired, rings 50 in test pattern 44 of FIG. 11 may be laterally offset from each other (i.e., rings 50 need not be concentric and may overlap each other).

Figure 12:
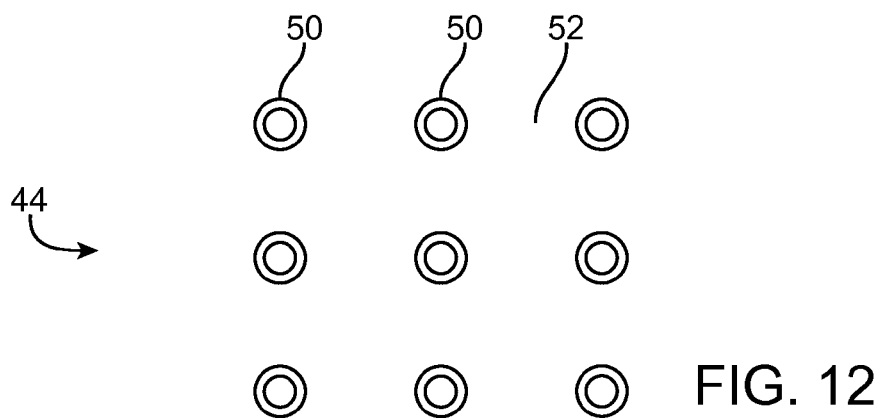
FIG. 12 is an illustrative lens test pattern having an array of rings in accordance with an embodiment of the present invention.
Figure 13:
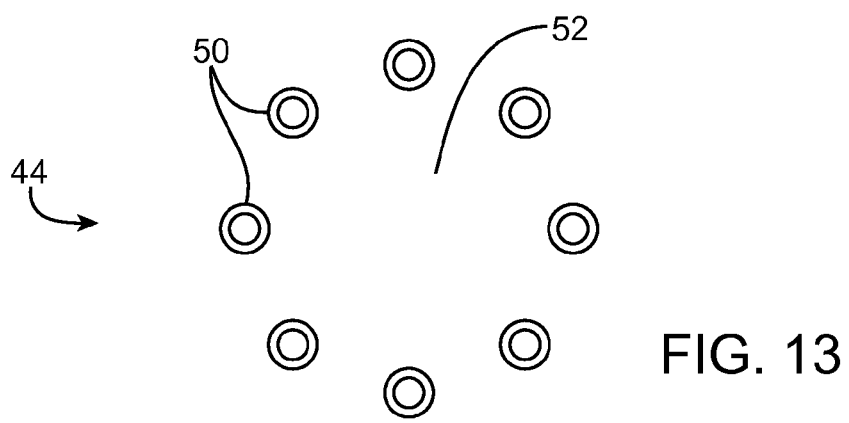
FIG. 13 is an illustrative lens test pattern having a circular array of illuminated ring-shaped test elements in accordance with an embodiment of the present invention.

FIG. 12 shows how test pattern 44 may include a rectangular array of ring-shaped test elements 50. Rectangular arrays may have any suitable numbers of rows and columns of test elements. The use of configurations with three or four rows and three or four columns of test elements is merely illustrative. As an example, test pattern 44 may contain one, two, three or more, five or more, ten or more, twenty or more, forty or more, 80 or more, or 160 or more test elements 50 organized in a rectangular array, in a pseudo-random pattern, in a circular pattern, in a spiral pattern, in a pattern having a circular or oval outline, in a pattern having straight edges, in a pattern having a combination of straight and curved edges, or in other suitable patterns. FIG. 13 shows an illustrative configuration in which test pattern 44 includes a set of ring-shaped test elements 50 organized in a circle.

Figure 14:
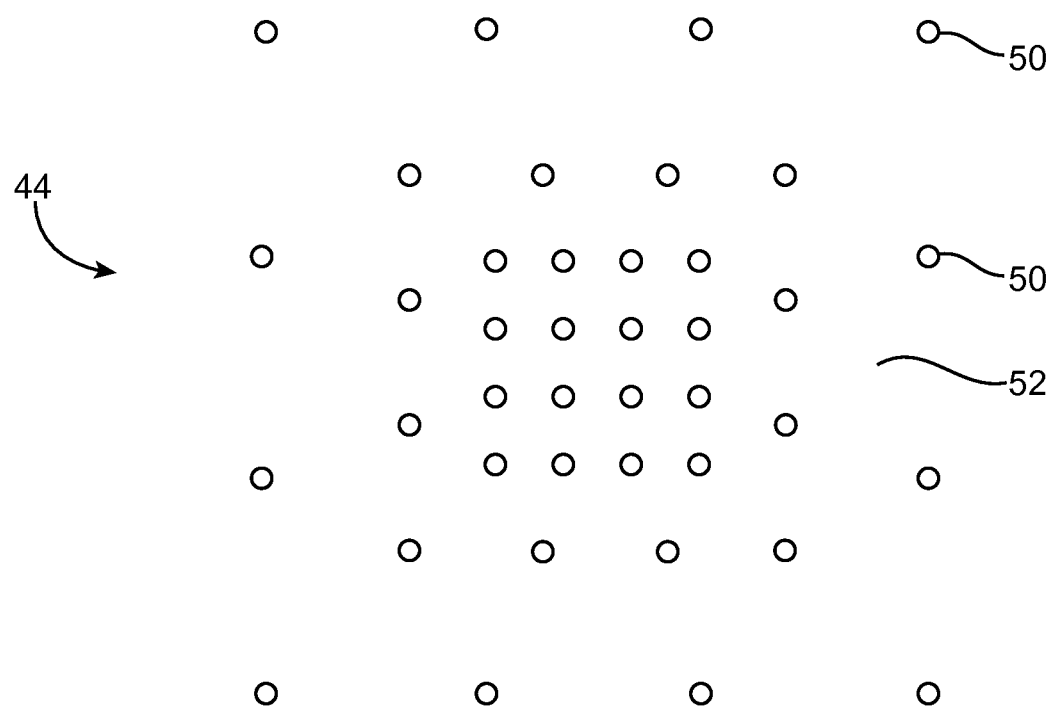
FIG. 14 is an illustrative lens test pattern having test elements that are distributed with an uneven density so as to concentrate test elements in areas of particular interest when testing a lens in accordance with an embodiment of the present invention.

Some portions of lens surface 30 (or other structures under test) may be of more interest than others. For example, central portions of lens surface 30 may have more impact on the performance of lens 28 than others. To ensure that the areas of most interest on lens 28 can be accurately evaluated, test pattern 44 may be provided with spots or other test pattern elements that are denser in some portions of pattern 44 than in others. As an example, test pattern 44 may have a layout of the type shown in FIG. 14. As shown in FIG. 14, the central portions of test pattern 44 may be provided with a greater concentration of spots 50 than the peripheral portions of test pattern 44. In general, the density of spots 50 in test pattern 44 may be varied as a function of lateral position within pattern 44, as a function of radial distance from the center of pattern 44, as a function of angular position within pattern 44, and/or as another function of position within pattern 44. The configuration of FIG. 14 in which spots 50 are unevenly distributed across test pattern 44 is merely illustrative.

Figure 15:
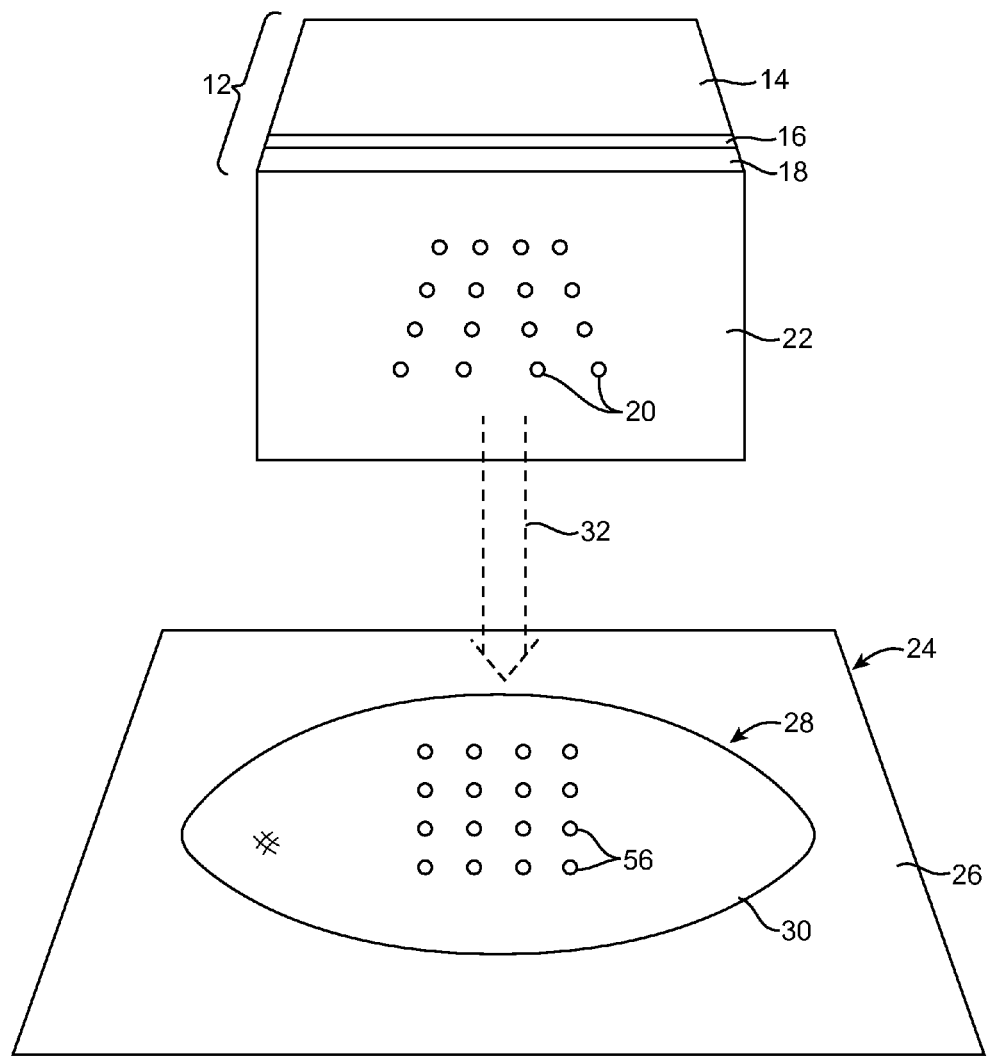
FIG. 15 is a diagram showing how a lens test pattern may be configured to fit the curvature of an optimal lens so that its reflection off a good lens will present a rectangular array pattern of evenly-spaced spots to the inspection system in accordance with an embodiment of the present invention.

Computing equipment 40 may use pattern recognition algorithms to evaluate pattern 44 on the surface of lens 28. To facilitate pattern recognition operations and/or to make it easier for a test system operator to manually ascertain whether a lens is satisfactory, it may be desirable to pre-distort pattern 44 so that the version of pattern 44 that appears on surface 30 of lens 28 has a regular and recognizable pattern. An example of this type of arrangement is shown in FIG. 15. As shown in FIG. 15, mask 18 of test pattern source may contain a pattern of openings 22 in opaque mask layer 22 that are configured so that the light spots that are produced in the test pattern have the appearance of the rectangular array of spots 56 on surface 30 of lens 28 when viewed using camera system 34. Other types of pattern distortion may be used, if desired. For example, pattern 44 may be configured so that a pattern of parallel lines is visible on lens surface 30, so that a grid with perpendicular straight lines is reflected from lens surface 30, so that a circular array of spots is produced on lens surface 30, or so that other desired patterns are produced on lens surface 30. By configuring pattern 44 at test pattern source 12 in this way, the process of acquiring and analyzing images of the test pattern on lens surface 30 may be simplified. For example, the ability of computing equipment 40 to implement spot counting algorithms, row spacing measurement algorithms, column spacing measurement algorithms, and other test pattern analysis algorithms may be enhanced. If desired, spots 50 may be preconfigured so that the spots in the reflected version of the spots all have the same intensity or have other regular patterns of intensities.

Figure 16:
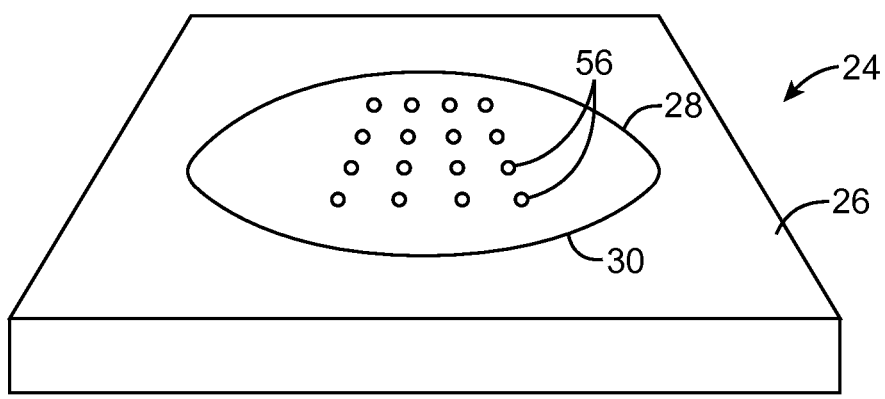
FIG. 16 is a diagram showing how an array of circular light spots or other test elements in a lens test pattern may be configured to partially cover the exposed surface of a lens under test in accordance with an embodiment of the present invention.

As shown in FIG. 16, the size of test pattern 44 can be configured so that test pattern 44 illuminates only a subset of the surface area of the surface to be tested. In the FIG. 16 example, test pattern 44 includes a four-by-four array of circular spots, leading to a four-by-four array of corresponding spots 56 on lens surface 30. The width and height of the array of spots 56 has been configured to fit within a central portion of the surface area of lens 30. This type of arrangement may be useful to avoid complications that may arise when evaluating spots on peripheral portions of lens surface 30, where spots may not land completely on surface 30 or may otherwise be difficult to detect.

Figure 17:
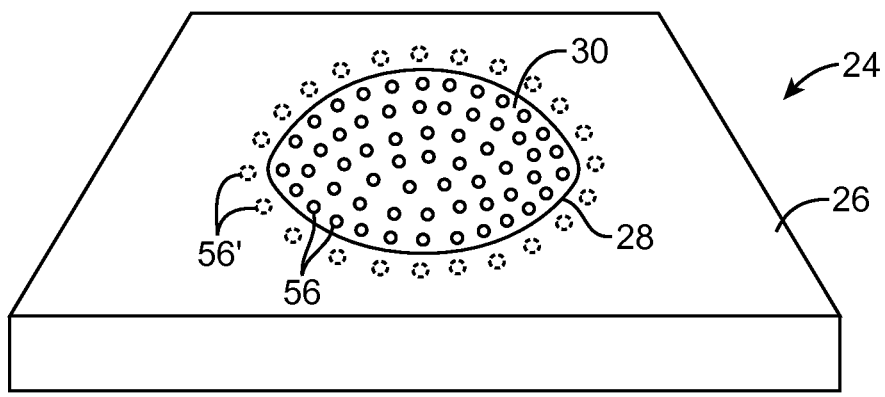
FIG. 17 is a diagram showing how an array of circular light spots or other test elements in a lens test pattern may be configured to illuminate an area that covers the entire exposed surface of a lens and additional surrounding areas in accordance with an embodiment of the present invention.

If desired, test pattern 44 may be oversized to ensure that spots 50 will completely cover lens surface 30. As shown in FIG. 17, for example, pattern 44 may be configured so that surface 30 is completely covered with spots 56. Some spots such as spots 56' will generally land outside of lens area 30 and may therefore not be imaged by camera system 34. Because the area covered by spots 56' and 56 is larger than necessary to cover lens area 30, misalignment of lens 28 can be tolerated without reducing the number of spots that appear on lens surface 30.

Using digital image processing, computing equipment 40 can evaluate the pattern of light that appears on surface 30 of lens 28 when illuminated with a test pattern from test pattern source 12. Image analysis with computing equipment 40 may be used to gather information on the size, shape, and location of lens 28.

Figure 18:
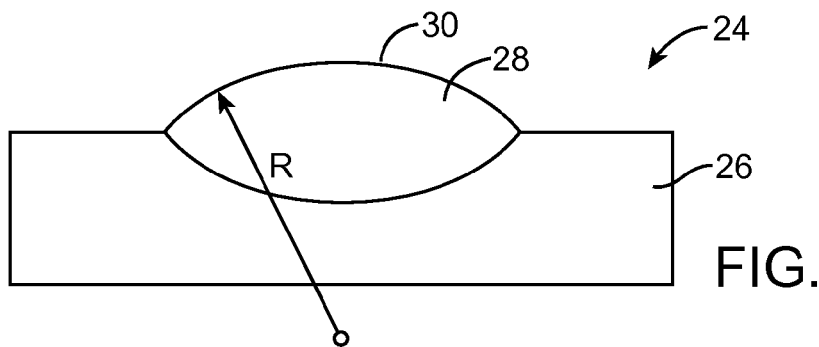
FIG. 18 is a cross-sectional side view of an illustrative lens that is characterized by a radius of curvature in accordance with an embodiment of the present invention.

As shown in FIG. 18, surface 30 of lens 28 may be characterized by a radius of curvature R (or other curvature metrics such as a more complex equation description or a surface described by a series of coordinates). During image processing operations with computing equipment 40, captured test pattern data may be analyzed to ascertain the value of R (or other curvature data) for the lens under test. If the value of R (or other surface shape data) is different than desired (e.g., in terms of offset distance, offset slope, or other metrics), appropriate action may be taken.

Figure 19:
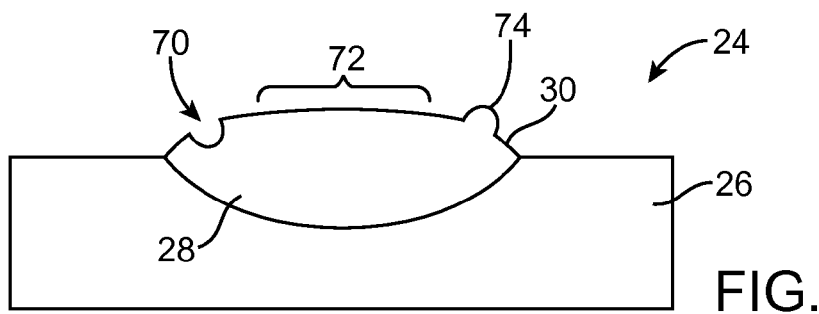
FIG. 19 is a cross-sectional side view of an illustrative lens with imperfections that may be detected by an optical inspection system in accordance with an embodiment of the present invention.

Lens 28 in the example of FIG. 19 contains three imperfections: recess (pit) 70, flat area 72, and protrusion (bump) 74. During image processing operations with computing equipment 40, the image data from camera system 34 may be evaluated to determine the location and area of pit 70, the location and area of flat region 72, and the location and area of bump 74. Other information on surface defects such as recesses, flat regions, and protrusions may be gathered if desired (e.g., recess curvature, recess shape, recess depth, protrusion curvature, protrusion shape, protrusion height, etc.).

Figure 20:
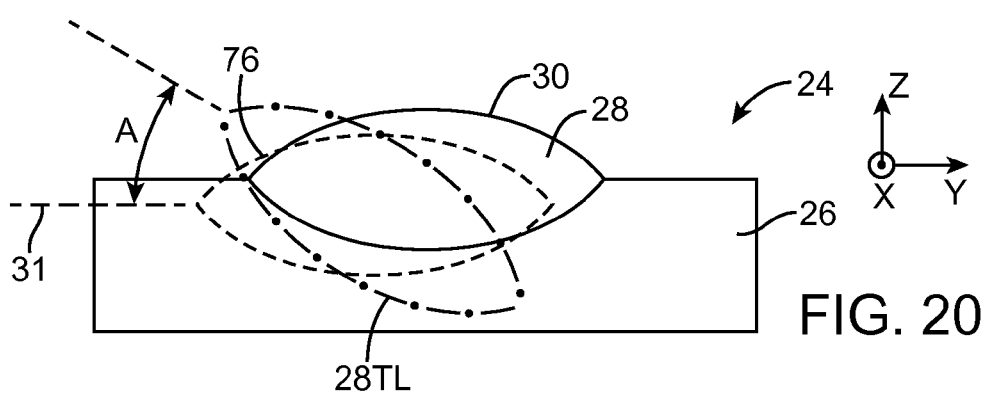
FIG. 20 is a cross-sectional side view of an illustrative lens showing how an optical inspection system may detect whether the lens has been offset from its desired location in accordance with an embodiment of the present invention.

FIG. 20 shows how lens 28 may have a location that is offset in dimensions X, Y, and/or Z from its desired location (location 76) or may have a location (shown as location 28TL) in which the lens is tilted at a non-zero angle A with respect to nominal horizontal axis 31 (i.e., the X-Y plane). Computing equipment 40 may perform image analysis operations on captured image data from camera system 34 to determine the magnitude of these lateral offsets and angular orientation deviations (i.e., non-zero lens tilts). In situations in which lens 28 and surface 30 are radially asymmetric, rotational angular offset information can be gathered. In situations in which lens 28 is nominally symmetric (i.e., when it is desired for lens 28 to be rotationally symmetric around its center), image analysis operations on the captured image data may be used to evaluate the degree of symmetry of lens 28 (e.g., to determine whether lens 28 is more asymmetric than desired).

Other lens parameters for lens 28 may be measured by using computing equipment 40 to perform image analysis on image data from camera system 34, if desired. Moreover, other types of structures may be evaluated by projecting spots 50 or other light patterns in test pattern 44 onto structures under test 24. Examples of other types of structures that may be evaluated in this way include other optical structures (e.g., camera windows, windows for sensors, status indicator light windows, optical port covers, display cover layers such as cover glass layers or layers of plastic in a display), device housing structures (e.g., a planar rear glass housing surface), device components (e.g., button members), glass portions of a track pad or mouse, plastic structures, ceramic structures, glass plates or other glass structures, or other device structures.

Figure 21:
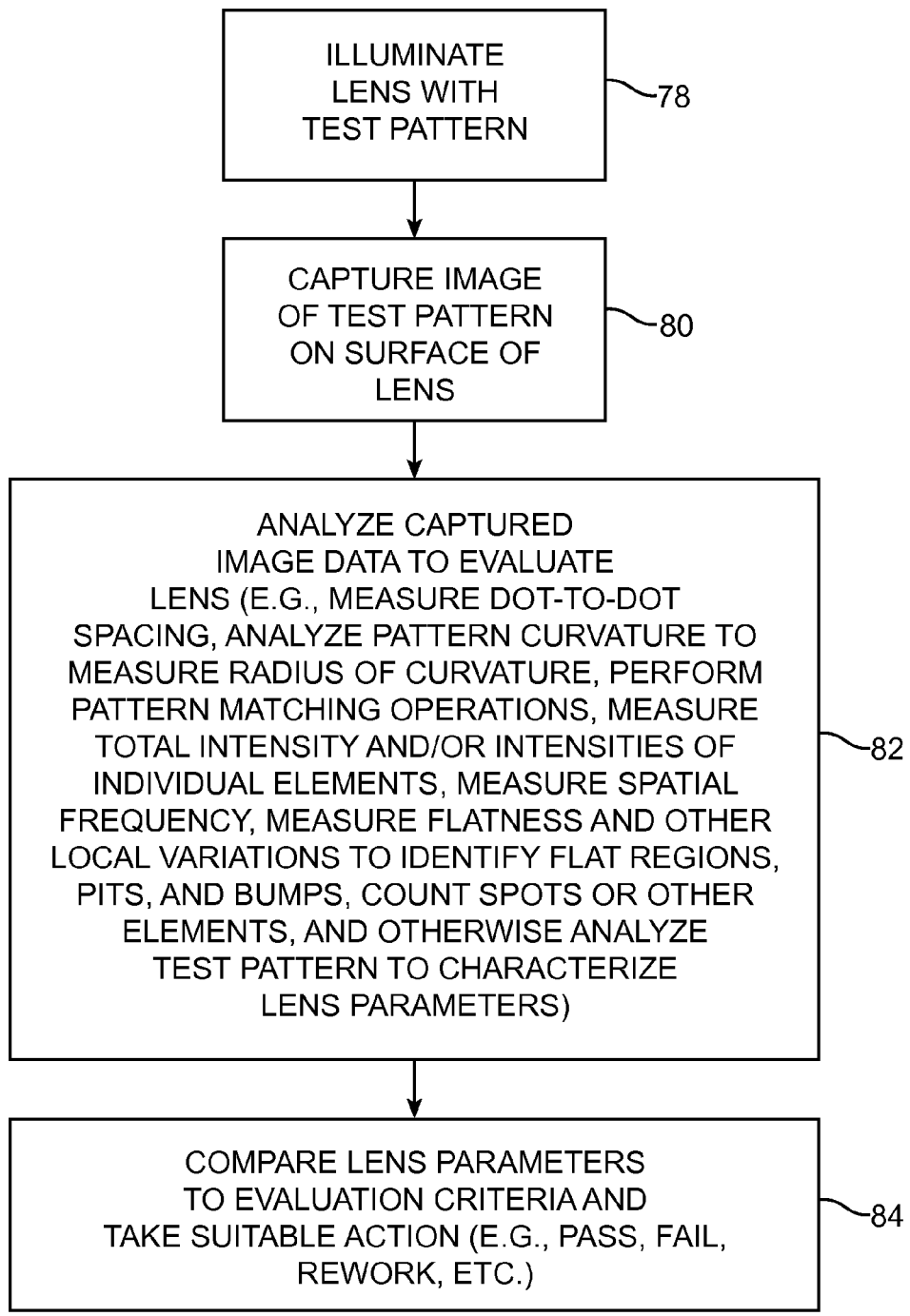
FIG. 21 is a flow chart of illustrative steps involved in evaluating a component such as a lens using an optical inspection system in accordance with an embodiment of the present invention.

Illustrative operations involved in using a system such as test system 10 of FIG. 1, 2, or 3 to evaluate a structure under test such as lens 28 are shown in FIG. 21.

At step 78, lens 28 may be illuminated with test pattern of light such as test pattern 44. Test pattern 44 may contain an array of spots such as spots 50 or other test elements (e.g., lines, circles, rings, crosses, squares, etc.). Spots 50 or other test elements may be organized in an evenly spaced array (e.g., a rectangular array or evenly-spaced circular pattern), may be pre-distorted to produce a regular shape when imaged on surface 30 of lens 28, may be distributed with an uneven density (e.g., so that portions of surface 30 that are relatively more important for proper lens functioning have a greater density of spots than portions of surface 30 that are relatively less important for proper lens functioning), may be configured to have desired intensity distributions, or may otherwise be distributed within pattern 44. If desired, the light that makes up test pattern 44 may have an out-of-band wavelength (e.g., a wavelength that does not lie in the transmission band for lens 28 such as visible light when lens 28 transmits infrared light or ultraviolet or infrared light when lens 28 transmits visible light). This may help to reduce undesired scattered light.

At step 80, while test pattern source 12 is producing test light for pattern 44 and while this test light is striking surface 30 of lens 28, camera system 34 may capture reflected light from surface 30 to acquire an image of test pattern 44 as it appears when reflected from surface 30. Captured image data from camera system 34 may be stored in storage in computing equipment 40. The storage of computing equipment 40 may also be used to store operating system code and code for an image analysis program. When the image analysis program code is executed using processing circuitry in computing equipment 40, computing equipment 40 may analyze the captured digital image data from camera system 34 to evaluate lens 28. Pattern recognition operations, spatial frequency measurements, intensity measurements, wavelength measurements (spectral data), and other measurements may be made.

Examples of parameters that may be evaluated include the spot-to-spot spacing in the test pattern (e.g., the apparent distance between respective spots 50), the curvature of lens 28 (e.g., the radius of curvature of surface 30), the total intensity of reflected pattern 44, the individual intensity of each reflected spot 50, the flatness of flat regions such as region 72 of FIG. 19, the shape, location, and other parameters associated with recess 70, the shape, location, and other parameters associated with protrusion 74, the number of spots 50 that fall in a particular portion of lens surface 30, the total number of distinct spots on surface 30, the number of spots per unit area (spot density) in each region of lens surface 30, the spacing between lines, crosses, rings, and other test elements, the straightness of reflected lines, and the concentricity of circular test elements in test pattern 44. During the operations of step 82, measured test pattern parameters may be processed to produce lens data. As an example, the spacing between spots may be used to compute a radius of curvature value for lens 28. As another example, the number of spots that is counted can be used to identify whether there are any surface defects such as flat areas, pits, or bumps and can therefore be converted into a defect count or other metric that corresponds to the degree of imperfection of surface 30. Multiple parameters may, if desired, be combined in ascertaining lens performance. For example, the number of spots counted and the statistical nature of the individual spot intensities can be analyzed together to determine whether or not any of the spots have merged (representing defects such as flat or recessed areas, etc.).

Following the data analysis operations of step 84, computing equipment 40 may compare the gathered test pattern data (raw and/or analyzed data) to lens evaluation criteria and suitable actions may be taken. Examples of actions that may be taken in response to determining that a lens has exhibited characteristics that do not satisfy predetermined criteria include discarding the lens (e.g., discarding a lens before or after assembling the lens into a finished component or device), reworking a partly competed assembly, repairing the lens, notifying an operator, making an entry in a data log, adjusting plastic molding equipment and other fabrication equipment to ensure that subsequent parts satisfy desired evaluation criteria, etc.

As an example of an illustrative comparison that may be performed during the operations of step 84 is comparing the number of spots that are detected by camera system 34 to an expected number of spots. If the number of spots that is measured by computing equipment 40 using camera system 34 deviates from the desired amount (e.g., if the number of spots measured is less than expected), it can be concluded that lens 28 contains an imperfection (e.g., a surface defect that causes spots to merge). As another example, if test element lines or rows/columns of spots are wavy or otherwise deviate from their expected positions by more than a predetermined amount, it can be concluded that surface 30 does not have an appropriate shape and suitable action may be taken. Defects associated with rotational position, linear offset, asymmetry, flatness, radius of curvature, spot-to-spot spacing, spot shape (or other test element shape), and other imperfections can also be identified by comparing expected test pattern characteristics to those measured using camera system 34.

Figure 22:
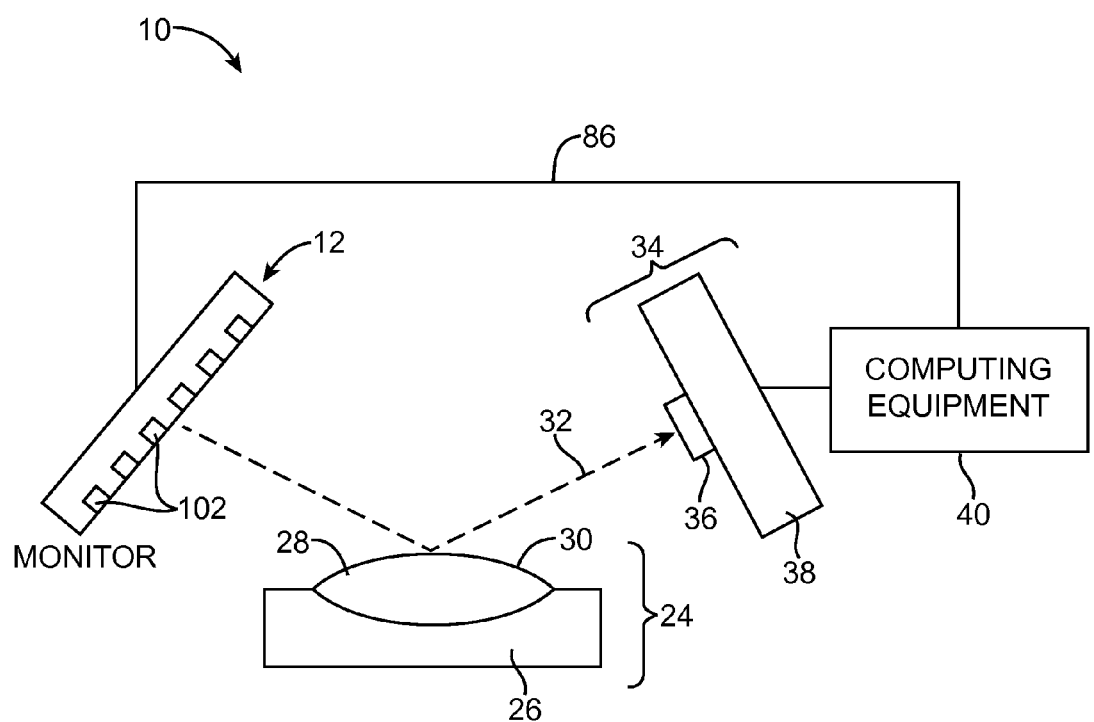
FIG. 22 is a diagram of an illustrative test system having a display that may be used to generate test patterns in accordance with an embodiment of the present invention.

FIG. 22 is a diagram of an illustrative test system having a display that may be used to generate test patterns. As shown in FIG. 22, system 10 may include a computer monitor or other display with an array of display pixels 102 that serves as test pattern generator 12. Display pixels 102 may be liquid crystal display pixels, plasma display pixels, light-emitting diode display pixels (e.g., organic light-emitting diode display pixels), cathode ray tube display pixels, or other suitable display pixels. Display pixels 102 may be configured to generate test patterns at suitable wavelengths of interest (e.g., infrared test patterns, red light, green light, blue light, or other visible light test patterns, ultraviolet light test patterns, etc.).

During testing with a test pattern, computing equipment 40 in system 10 or an operator may detect defects or areas of interest for further investigation on lens surface 30. Based on operator input or real time analysis by computing equipment 40, the test pattern displayed by the array of display pixels 102 in test pattern generator 12 may be updated by computing equipment 40. Computing equipment 40 may communicate with test pattern generator 12 via path 86. Modifying the test pattern in this way may help system 10 to accurately identify defects. For example, system 10 may initially use a test pattern with an array of widely spaced spots. If testing with the widely spaced spot array reveals localized areas of potential imperfections, computing equipment 40 may direct display 12 to generate a fine-pitched pattern for testing the localized areas of interest. System 10 may analyze image data that is captured using the fine-pitched pattern to ensure that the localized areas are free of defects.

Figure 23:
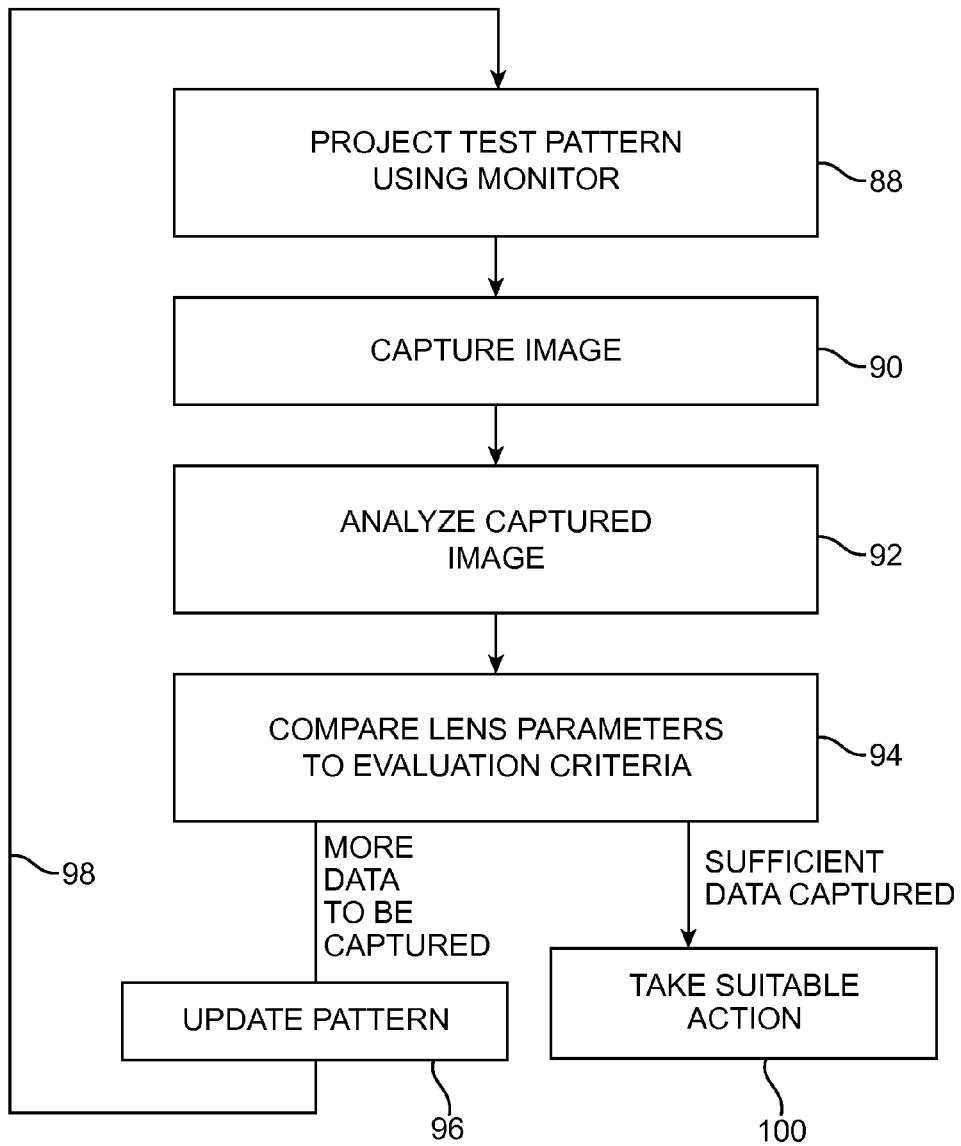
FIG. 23 is a flow chart of illustrative steps involved in using a test system of the type shown in FIG. 22 in accordance with an embodiment of the present invention.

A flow chart of illustrative steps involved in using a test system of the type shown in FIG. 22 is shown in FIG. 23.

At step 88, a display-based test pattern generator such as display 12 of FIG. 22 may project a test pattern for testing surface 30 of lens 28.

At step 90, computing equipment 40 may use camera system 34 to capture an image of the test pattern.

At step 92, computing equipment 40 may analyze the captured image. During the operations of step 94, computing equipment 40 can compare the captured image data to evaluation criteria (expected radius of curvature, expected number of spots, expected reflected line shape, etc.) to determine whether additional testing data is desired. If more data is to be captured, the test pattern that is to be used may be updated. For example, computing equipment 40 may (automatically, or in response to a determination that more detailed testing is desired) update the test pattern so that more finely pitched spots are used (globally and/or locally). Processing may then loop back to the operations of step 88, as indicated by line 98.

In response to a determination by computing equipment 40 at step 94 that sufficient lens data has been captured, computing equipment 40 may take a suitable action at step 100 based on a comparison of the acquired lens data to predetermined evaluation criteria (e.g., to discard or rework the lens if faulty, to incorporate the lens into a product if not faulty, etc.).

Figure 24:
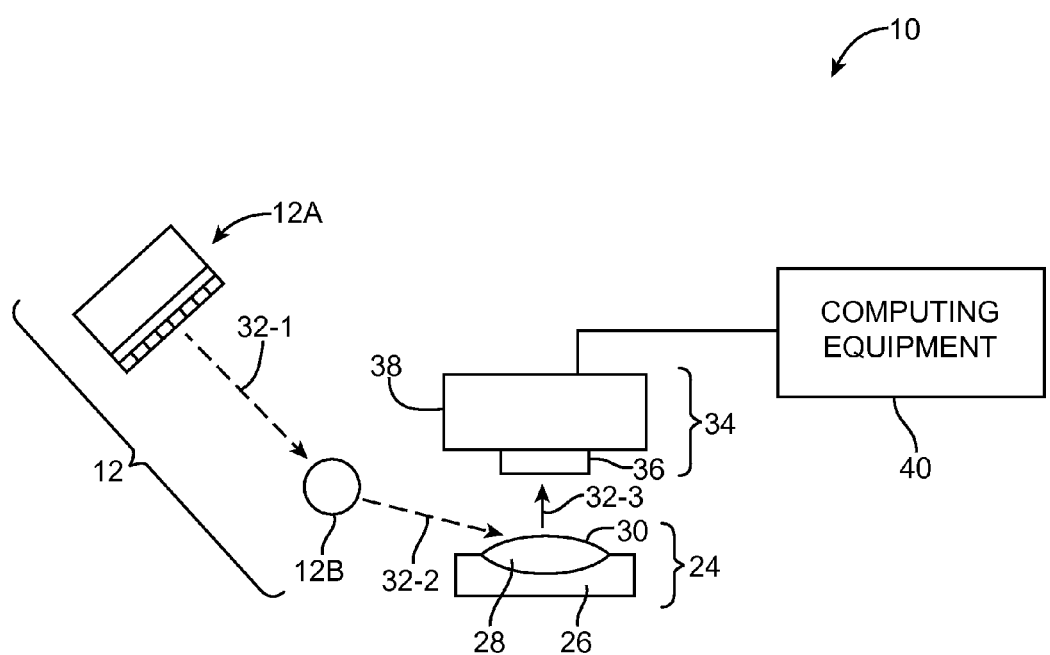
FIG. 24 is a diagram of an illustrative lens inspection system having test pattern generation equipment that includes an ancillary optical component to help direct light onto a lens surface during testing in accordance with an embodiment of the present invention.

In some configurations, it may be challenging to direct light 32 directly onto surface 30 of lens 30 (e.g., in configurations in which camera system 34 has been positioned relatively close to surface 30). To help direct light 32 onto surface 30, test pattern generator 12 may, if desired, include mirrors or focusing lenses to help direct light 32 onto lens 28. FIG. 24 is a diagram of an illustrative lens inspection system having test pattern generation equipment 12 that includes main portion 12A for generating test pattern light 32-1 and that includes an ancillary optical component such as a mirror and/or lens system (component 12B). Ancillary optical system 12B may be used to redirect light 32-1 towards lens 28 (see, e.g., redirected light 32-2). Light 32-2 may reflect from surface 30 and may be passed to camera system 34 as reflected light 32-3.

Figure 25:
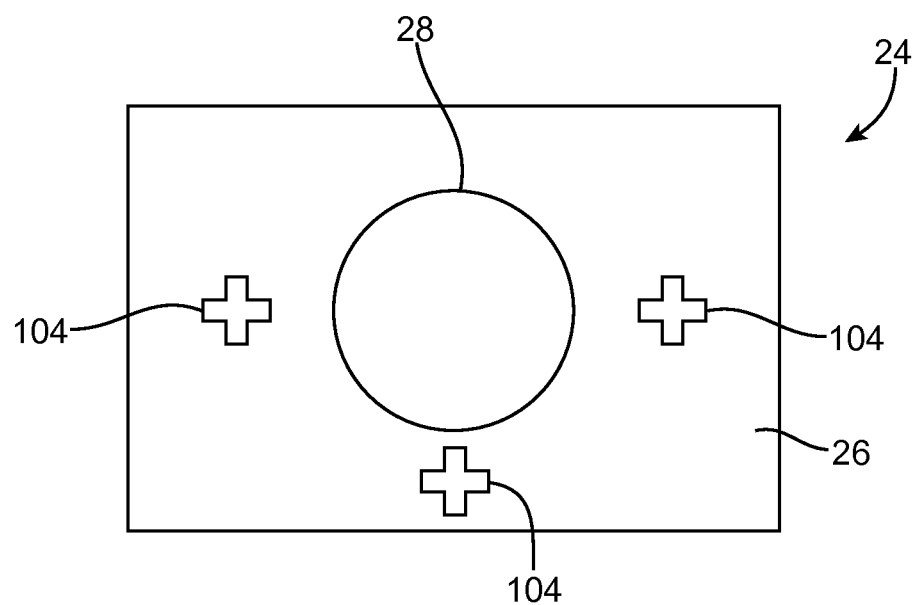
FIG. 25 is a top view of an illustrative lens in a support structure with fiducials in accordance with an embodiment of the present invention.

If desired, alignment marks such as fiducials 104 of FIG. 25 may be incorporated into the structures under test (e.g., as part of a lens housing, part of a structure that is temporarily holding a test component, etc.). In the example of FIG. 25, fiducials 104 have been incorporated into support structures 26 (e.g., temporary or finished lens housing structures for lens 28). Computing equipment 40 may use camera system 34 to captured information on fiducials 104 to determine the location of support structure 26 relative to lens 28 (e.g., to produce lens offset information).

Figure 26:
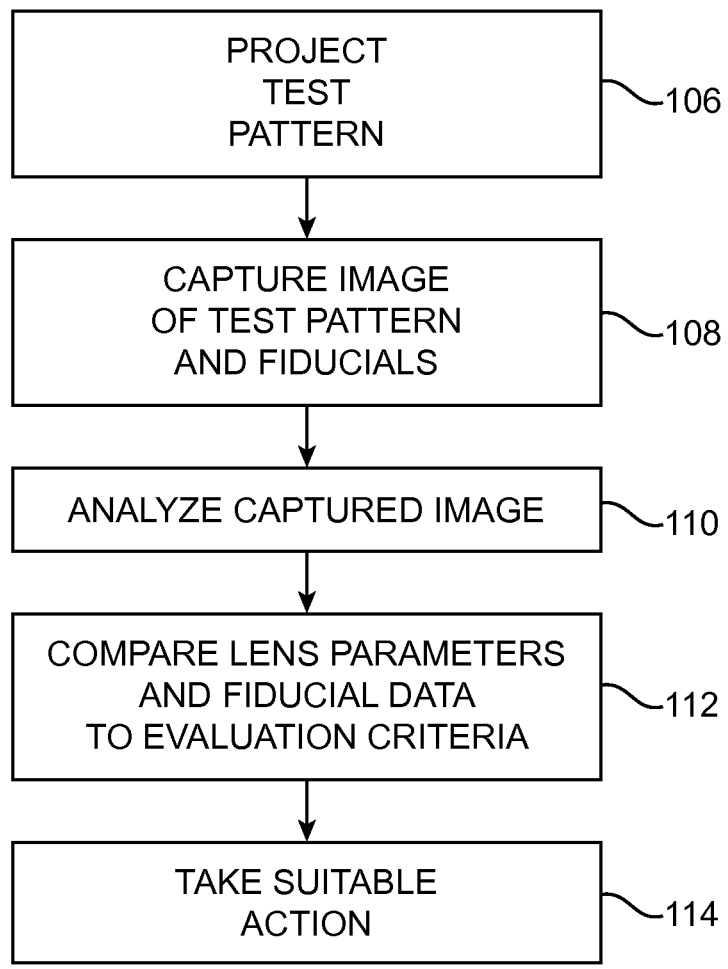
FIG. 26 is a flow chart of illustrative steps involved in using a test system to process captured image data that includes information on fiducials in accordance with an embodiment of the present invention.

FIG. 26 is a flow chart of illustrative steps involved in using a test system to process captured image data that includes information on fiducials.

At step 106, test pattern generator 12 may project a test pattern for testing surface 30 of lens 28.

At step 108, computing equipment 40 may use camera system 34 to capture an image of the test pattern that has reflected from lens surface 30 and may use camera system 34 to capture an image of fiducials 104 or other information on the position of structures 26.

At step 110, computing equipment 40 may analyze the captured image data. During the operations of step 110, computing equipment 40 can compare the captured image data to evaluation criteria (lens characteristics such as expected radius of curvature, expected number of spots, expected reflected line shape, and offset characteristics such as the offset of fiducials 104 and therefore structures 26 from the center of lens 28 in dimensions X, Y, and Z).

At step 112, computing equipment 40 may compare captured lens and fiducial information to evaluation criteria (e.g., to determine whether surface 30 of lens 28 contains imperfections and/or to determine whether lens 28 is offset by more than an acceptable amount relative to fiducials 104). In response to this comparison, suitable action may be taken at step 114 (e.g., to adjust the manufacturing process, to rework faulty components, to discard lens assemblies with faults, to accept for further use parts that pass testing, etc.).

Figure 27:
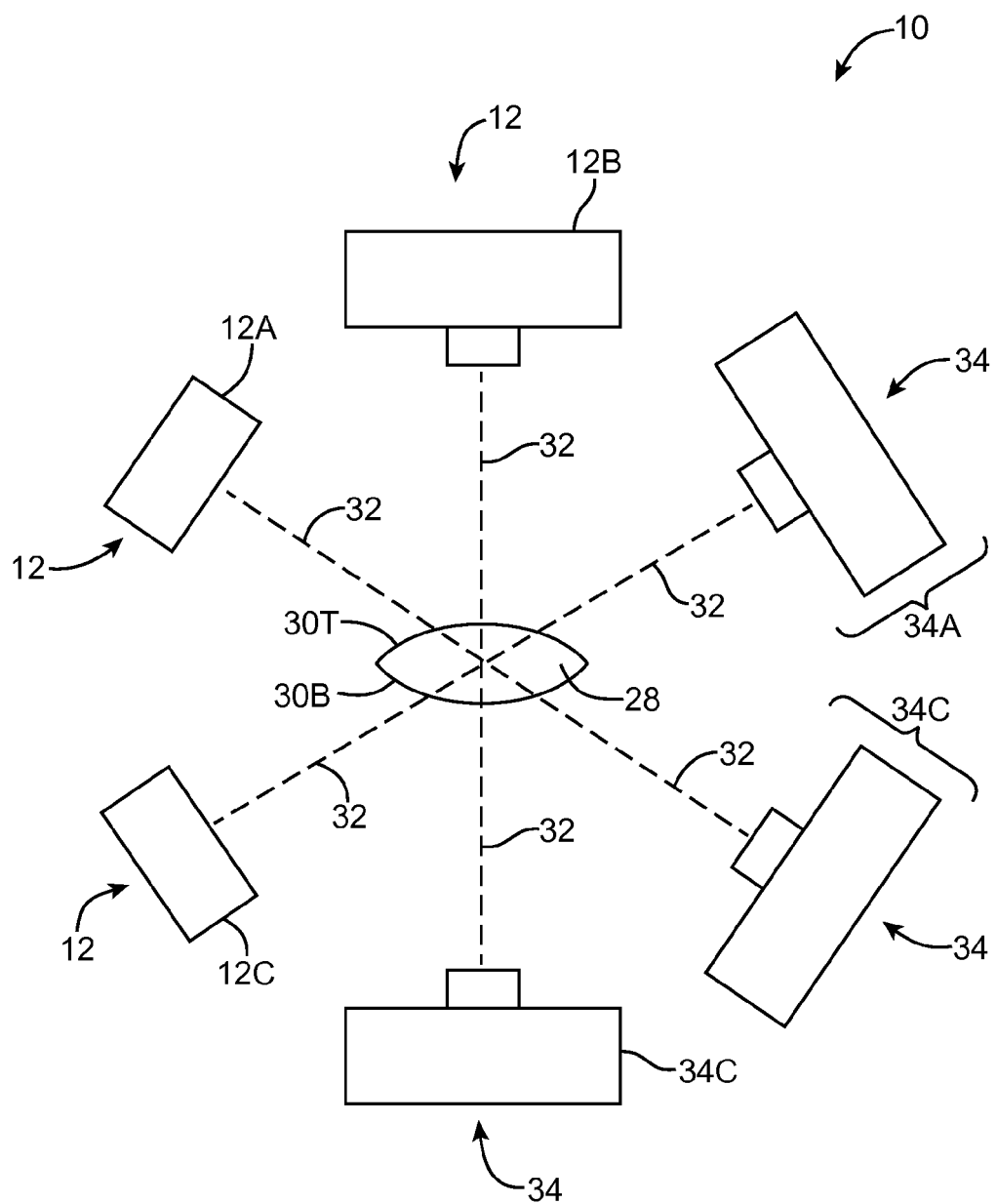
FIG. 27 is a diagram of an illustrative test system showing how test light may be applied to the front and rear of a lens and showing how camera systems or other detectors may be used in gathering front-side reflections, backside reflections, and transmitted light to determine whether a lens contains faults in accordance with an embodiment of the present invention.

As shown in FIG. 27, system 10 may include equipment for testing the front and rear of lens 28 and for testing for internal lens defects in lens 28. System 10 may, for example, include test light generation equipment such as test pattern generator 12A, test pattern generator 12B, and test pattern generator 12C (as examples). Camera equipment 34 may include one or more camera systems such as camera systems 34A, 34B, and 34C for gathering light that has been reflected off of lens 28 and/or that has been transmitted through lens 28.

To facilitate test measurements where light is being scattered off of a surface of lens 28, test pattern generator equipment 12 may use a wavelength of light that is weakly transmitted by lens 28 (i.e., an out-of-band wavelength of light that is absorbed by lens 28). To facilitate test measurements where light is being transmitted through lens 28, test pattern generator equipment 12 may use an in-band wavelength of light (i.e., a wavelength that is well transmitted though lens 28).

Light reflections may be made off of the exposed side of a lens surface and/or from the internal side of a lens surface. Combinations of lens surface reflection measurements and lens transmission measurements may be made in characterizing lens 28. As an example, equipment 12A may generate a test pattern that is captured by camera system 34A for inspecting upper lens surface 30T and/or lower lens surface 30B. Equipment 12C may generate a test pattern that is captured by camera system 34C for inspecting lower lens surface 30B of lens 28 and/or upper lens surface 30T. Equipment 12B may generate a test pattern (e.g., test light) that is captured by camera system 34B. Light from equipment 12B (and or light from other sources such as sources 12A and 12B) that passes through lens 28 and that is captured by a detector such as camera system 34C may be used in analyzing lens transmission performance (e.g., to monitor for the presence of lens voids or other bulk defects in lens 28). Bulk defects may also be detected using camera systems 34A and 34C (e.g., by focusing on the middle of lens 28).

To facilitate image analysis on captured image data from camera systems 32 of FIG. 27, the wavelengths of light that are analyzed may be filtered (e.g., upon light transmission by test pattern generation equipment 12 and/or upon light detection using camera systems 32). As an example, consider a lens that transmits infrared light but only weakly transmits visible light. In this situation, surface defects can be analyzed by using camera system 32 to capture bluish visible light from the lens surface. Light at this wavelength tends to be absorbed by lens 28, so that light reflections that travel through the bulk material of lens 28 are suppressed. Bulk defects can be detected by using camera system 32 (e.g., camera system 34C to capture light emitted by sources such as sources 12A and/or 12B) to capture light at longer wavelengths (e.g., visible light at green wavelengths or longer visible wavelengths, infrared light, etc.), because this light passes through lens 28 readily. Digital image processing techniques may be used to discriminate between captured wavelengths. Sources 12 and camera system 34 may also use optical filtering or other filtering schemes to discriminate between light at different wavelengths.

If desired, a temporary coating may be added to lens 28 to help detect defects. As an example, a temporary light-absorbing or reflecting coating may be added to one or more lens surfaces such as surfaces 30T and 30B. The coating may be formed from a water-soluble or alcohol-soluble material (as examples). The presence of the coating may help separate interior lens reflections from surface lens reflections. Lens 28 may, if desired, have a permanent coating that may facilitate the separation of interior lens reflections from surface lens reflections. In response to a determination that the interior of lens 28 has too many voids (e.g., bubbles), further analysis may be halted and the lens may be discarded or reworked.

If desired, lens rear surfaces such as lens surface 30B of FIG. 27 may be examined by capturing an image with a front-side camera system. For example, light that is supplied to the interior of lens surface 30B may be captured using a front-side camera system such as camera system 34A. In this type of configuration, test pattern 44 may be preconfigured so that the pattern of spots or other test elements that is observed in the captured image data will have a regular rectangular array shape or other known shape to facilitate fault detection.

In general, camera systems 32 may focus on the front or rear of a given lens or may focus on the middle (bulk portions) of the lens. Camera system 32A may, for example, focus on front surface 30T to examine surface 30T for defects, may focus on rear surface 30B to examine surface 30B for defects, and/or may focus in the middle of lens 28 between surfaces 30T and 30B to examine lens 28 for bulk defects (e.g., voids).

Figure 28:
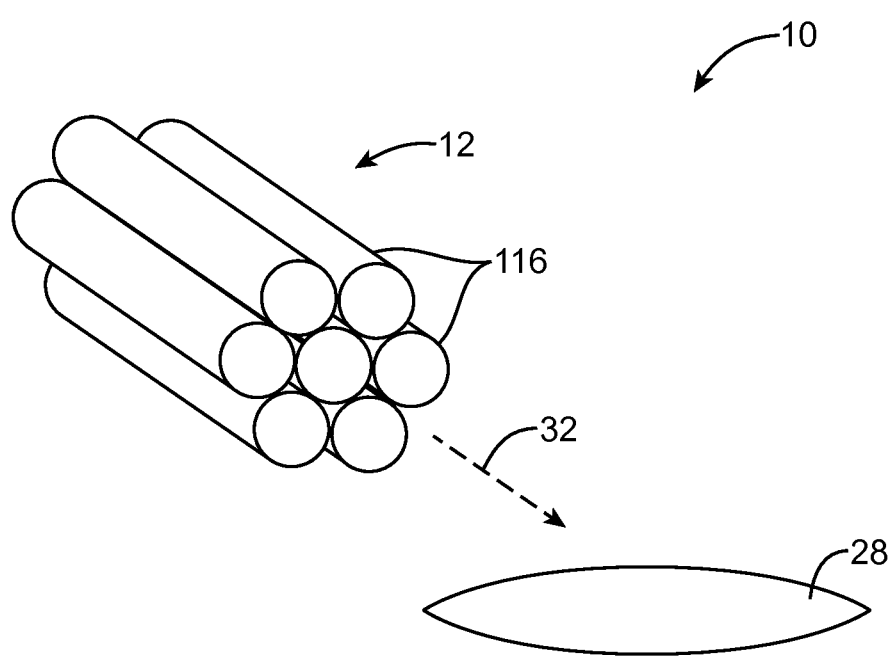
FIG. 28 is a perspective view of a portion of an illustrative test system in which a test pattern generator has been formed using fiber optic structures in accordance with an embodiment of the present invention.

FIG. 28 is a perspective view of a portion of an illustrative test system in which a test pattern generator has been formed using fiber optic structures. As shown in FIG. 28, test pattern source 12 may include one or more optical fibers such as fibers 116. Fibers 116 may be organized as a fiber bundle or may be implemented using one or more individual fibers. Fiber structures 116 may be used to form a pencil-shape source suitable for placement close to compact lenses.

Figure 29:
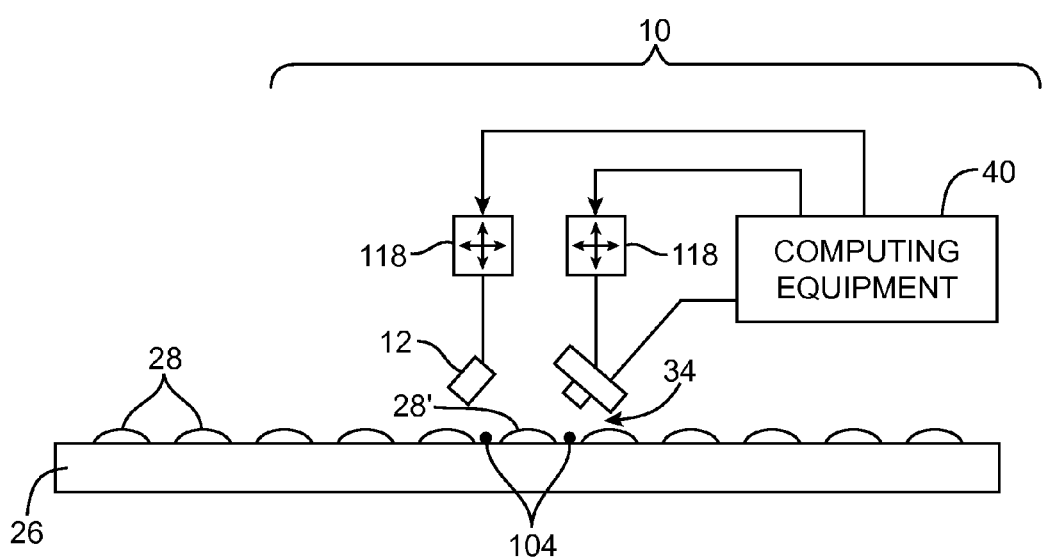
FIG. 29 is a diagram showing how an inspection system may be used to inspect a sheet of lenses in accordance with an embodiment of the present invention.

As shown in FIG. 29, lenses 28 may be mounted in a support structure such as support sheet 26 (e.g., following an injection molding operation). Test system 10 may include computer-controlled positioning equipment such as positioning equipment 118 (e.g., positioners in robotic inspection equipment). Computing equipment 40 may be used to control the positions of system components such as test pattern source 12 and/or camera system 34 using positioners 118. This may allow system 10 to inspect individual lenses on sheet 26 such as lens 28' in the example of FIG. 29. System 10 may step through each lens on sheet 26 to test a batch of lenses. Sheet 26 may be a temporary support structure. Following testing using system 10, lenses that pass inspection may be assembled into lens housings. Fiducials 104 may be arranged around lenses such a lens 28' (e.g., as part of sheet 26).

Figure 30:
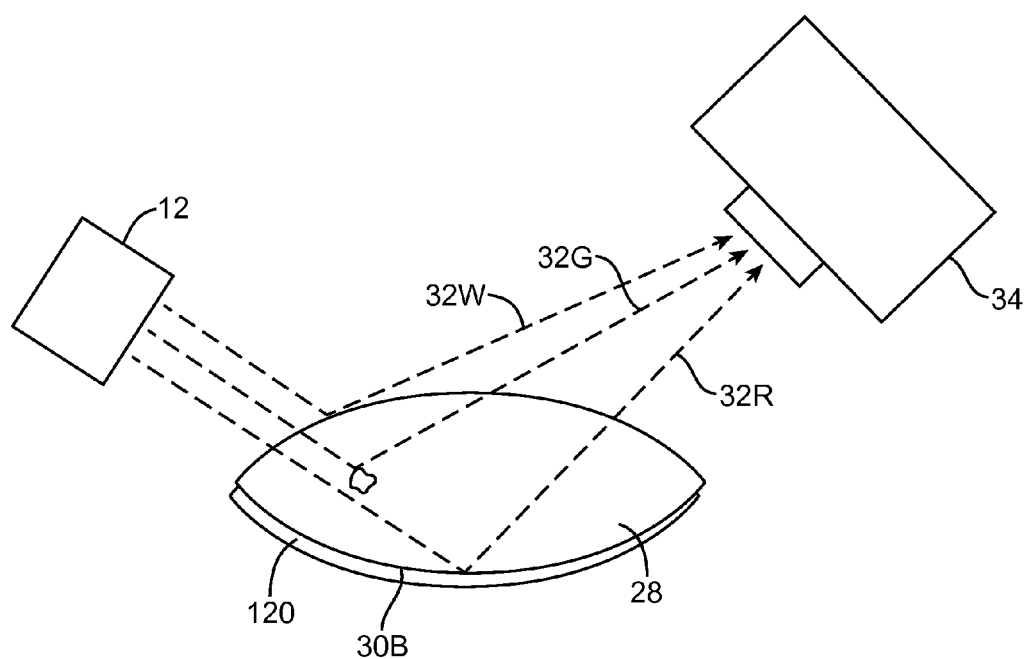
FIG. 30 is a cross-sectional side view of an illustrative lens showing how light of three different colors may be captured by a camera system during lens inspection operations in accordance with an embodiment of the present invention.

FIG. 30 is a cross-sectional side view of an illustrative lens showing how light of different colors may be captured by a camera system during lens inspection operations. Test pattern source 12 may emit white light (as an example). The white light pattern from source 12 may reflect off of top surface 30T of lens 28 and may be captured as white reflected light 32W by camera system 34. The bulk material of lens 28 may tend to absorb blue light, so that light such as light 32G that is reflected from voids or other bulk defects may have a greenish color. Surface reflections from the inside of lower surface 30B of lens 28 may be colored similarly or may be provided with a different color using a coating (e.g., a temporary coating) such as coating 120. As an example, coating 120 may be configured to impart a red color to reflected light from test pattern source 12, so that reflected light 32R is red.

Using this type of scheme, camera system 34 may be able to discriminate between reflections from surface 30T (which appear white), reflections form bulk material in lens (which appear green), and reflections from the inside of rear surface 30B (which appear red). Other combinations of colors may be produced by using a different light spectrum for the emitted light from light source 12, by using different bulk material for forming lens 28, and/or by forming coatings with different spectral properties on one or more surfaces of lens 28. The example of FIG. 30 is merely illustrative.

The foregoing is merely illustrative of the principles of this invention and various modifications can be made by those skilled in the art without departing from the scope and spirit of the invention.

What is claimed is:

1. A method of evaluating a lens having a lens surface, comprising:
    applying a temporary reflective coating to the lens;
    with a test pattern source, generating a test pattern of light that reflects off of the temporary reflective coating;
    with a camera system, capturing an image of the reflected test pattern;
    with computing equipment, evaluating the lens by processing the captured image of the reflected test pattern; and
    after capturing the image of the reflected test pattern, removing the temporary reflective coating from the lens.

2. The method defined in claim 1 wherein generating the test pattern comprises generating a plurality of illuminated test elements with a dark background.

3. The method defined in claim 1 wherein generating the test pattern comprises generating an array of light spots.

4. The method defined in claim 1 wherein generating the test pattern comprises generating concentric rings of light.

5. The method defined in claim 1 wherein generating the test pattern comprises generating an array of crosses.

6. The method defined in claim 1 wherein generating the test pattern comprises generating a test pattern that has light spots, wherein the light spots have a first density in a first portion of the test pattern and have a second density in a second portion of the test pattern, and wherein the second density is different than the first density.

7. The method defined in claim 1 wherein generating the test pattern comprises generating a circular pattern of test elements.

8. The method defined in claim 1 wherein generating the test pattern comprises generating a plurality of illuminated rings.

9. The method defined in claim 1 wherein generating the test pattern comprises generating a test pattern sufficiently large to cover the surface of the lens.

10. The method defined in claim 1 wherein evaluating the lens by processing the captured image of the reflected test pattern comprises counting spots in the captured image.

11. The method defined in claim 1 wherein evaluating the lens by processing the captured image of the reflected test pattern comprises determining a radius of curvature value for the lens.

12. The method defined in claim 1 wherein evaluating the lens by processing the captured image of the reflected test pattern comprises measuring spot-to-spot distances.

13. The method defined in claim 1 wherein evaluating the lens by processing the captured image of the reflected test pattern comprises measuring line curvatures.

14. The method defined in claim 1 wherein evaluating the lens by processing the captured image of the reflected test pattern comprises processing the captured image to identifying flat portions of the lens surface.

15. The method defined in claim 1 wherein evaluating the lens by processing the captured image of the reflected test pattern comprises processing the captured image to identify protrusions in the lens surface.

16. The method defined in claim 1 wherein evaluating the lens by processing the captured image of the reflected test pattern comprises processing the captured image to identify recesses in the lens surface.

17. The method defined in claim 1 wherein the test pattern includes an array of test elements and wherein evaluating the lens by processing the captured image of the reflected test pattern comprises processing the captured image to individually analyze the test elements in the array.

18. The method defined in claim 1 further comprising determining whether the lens satisfies predetermined criteria using the processed captured image.

19. The method defined in claim 1 further comprising:
   after removing the temporary reflective coating from the lens, assembling the lens into an electronic device.

20. A lens testing system for testing a lens having a lens surface, comprising:
   a test pattern source configured to generate a test pattern of light;
   a camera system configured to capture an image of the test pattern reflected from the lens surface;
   computing equipment configured to evaluate the lens by processing the captured image of the reflected test pattern, wherein the test pattern source comprises:
      a light source; and
      an opaque mask containing a pattern of openings that allow the light to pass through the opaque mask to form the test pattern; and
   a diffuser between the light source and the opaque mask.

21. The lens testing system defined in claim 20 wherein the openings in the opaque mask are configured to form an array of spots.

\* \* \* \* \*